United States Patent [19]

Grivas et al.

[11] Patent Number: 4,474,646

[45] Date of Patent: Oct. 2, 1984

[54] PROCESS FOR VINYL AROMATIC MONOMER POLYMERIZATION INHIBITION

[75] Inventors: John C. Grivas, Oak Lawn; Myong-Gi A. Park, Dolton, both of Ill.

[73] Assignee: The Sherwin-Williams Company, Cleveland, Ohio

[21] Appl. No.: 393,006

[22] Filed: Jun. 28, 1982

[51] Int. Cl.$^3$ .......................... B01D 3/34; C07C 7/05; C07C 7/20
[52] U.S. Cl. .......................................... 203/9; 203/65; 585/4; 585/860
[58] Field of Search ........................................ 585/1–5, 585/800, 860; 203/9, 8, 6, 7, 65, 51, 56; 208/48 AA

[56] References Cited

U.S. PATENT DOCUMENTS

| | | | |
|---|---|---|---|
| 2,304,728 | 12/1942 | Boyer et al. | 203/9 |
| 2,526,567 | 10/1950 | Drake et al. | 203/9 |
| 2,556,030 | 6/1951 | Coulter et al. | 203/9 |
| 4,033,829 | 7/1977 | Higgins et al. | 203/9 |
| 4,132,602 | 1/1979 | Watson | 203/9 |
| 4,132,603 | 1/1979 | Watson | 203/9 |

*Primary Examiner*—Wilbur L. Bascomb, Jr.
*Attorney, Agent, or Firm*—James V. Tura; Robert E. McDonald

[57] ABSTRACT

This invention is directed to the use of mixtures of a polymerization inhibitor in the distillation of readily polymerizable vinyl aromatic monomers and more specifically to the use of mixtures containing 2,6-dinitro-4-halophenols as polymerization inhibitors for vinyl aromatic monomers such as styrene and vinyl benzenes. The invention comprises the process of subjecting the vinyl aromatic monomers to distillation temperatures in the presence of mixtures containing 2,6-dinitro-4-halophenols to inhibit polymerization.

5 Claims, No Drawings

PROCESS FOR VINYL AROMATIC MONOMER POLYMERIZATION INHIBITION

BACKGROUND OF THE INVENTION

This invention is directed to a process for the distillation of readily polymerizable vinyl aromatic monomers such as styrene, substituted styrene and vinyl benzenes, and more specifically to a process for the distillation of vinyl aromatic monomers wherein the degree of polymerization of the monomer is substantially reduced, under distillation conditions, by the presence of small but effective amounts of mixtures containing 2,6-dinitro-4-halophenols (Structure I).

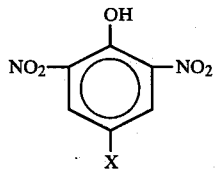

STRUCTURE I wherein X equals flourine, chlorine, bromine or iodine.

It is generally known that vinyl aromatic compounds such as monomeric styrene and the alkylated sytrenes such as methyl styrene, ethyl styrene, etc. are easily polymerized under distillation conditions and more particularly the rate of polymerization of the monomers increases substantially at increased temperatures. Many of the vinyl aromatic monomers available commercially, generally contain a variety of impurities and therefore these monomers need be purified, i.e. by distillation, to obtain the substantially pure monomer, i.e. styrene. As indicated, the purification and separation of these impurities from monomers are generally accomplished by distillation. Thus, in order to prevent polymerization of the monomers during the distillation purification process, various compounds are added to the distillation as polymerization inhibitors.

For example, sulfur has been employed as a polymerization inhibitor. However, sulfur while being a reasonable effective inhibitor, has many disadvantages in that the waste materials formed are highly contaminated and therefore are of little or no value. Other inhibitors include alkylated catechols, hydroquinone, and a number of the halogen-substituted cresols such as 2-chloro-6-nitro-paracresol, 2-bromo-6-nitro- paracresol and mixtures of these materials as specifically taught in U.S. Pat. No. 4,132,602. In addition, other inhibitors include 3-nitro-2,5-cresotic acid and 3-nitro-2,5-cresotaldehyde as taught in U.S. Pat. No. 4,132,601. Still further, other vinyl inhibitors include the halogenated toluenes such as 4-halo-3,5-dinitrotoluene as taught in U.S. Pat. No. 4,132,603 and the nitrocresols as taught in U.S. Pat. No. 4,086,147.

While most of these compounds are effective for inhibiting the polymerization of vinyl aromatic compounds, not all of the compounds have been successful as polymerization inhibitors under the stringent conditions of distillation. It was found that notwithstanding the use of these inhibitors, the distillation of crude styrene, for example, resulted in products containing substantial quantities of polymeric material which is difficult to separate from the monomer.

More important, a number of the vinyl aromatic inhibitors have high melting points, e.g. dinitro paracresol has a melting point of about 85° C. and therefore is transported as a solid. Thus, before using dinitro paracresol, it must be dissolved in solvents, e.g. ethyl benzene which subsequently requires separation. This requires additional equipment and adds to the process time and increased cost. Moreover, it is necessary to add these inhibitors as solutions of ethyl benzene to the monomer, e.g. styrene, since dinitro paracresol can not be held at temperatures greater than 85° C. for any period of time due to the potential danger of side reactions and because of the explosive nature of the compound.

In comparison, mixtures of 2,6-dinitro-4-halophenols and 2,6-dinitro-4-ethylphenol have lower melting points and therefore can be transported as a liquid and metered directly into the process requiring no separation or other equipment.

Accordingly, it is an object of this invention to provide an effective polymerization inhibitor for distillation of vinyl aromatic compounds particularly styrene, and vinyl benzenes at elevated temperatures, which are easy to use and less costly. It is another object of this invention to provide an effective polymerization inhibitor for styrene and vinyl benzenes which are liquid at ambient temperatures and can be added directly to the distillation process without any prior treatment or handling.

These and other objects of the invention will become apparent from a further and more detailed description of the invention as follows. Specifically, this invention relates to a process for distilling polymerizable vinyl aromatic monomers such as styrene, substituted styrenes, alkyl benzenes and the like by subjecting the vinyl aromatic monomers to distillation temperatures in the presence of small but effective amounts of mixtures of 2,6-dinitro-4-halophenols, e.g. 2,6-dinitro-4-chloro, 2,6-dinitro-4-bromo, or 2,6-dinitro-4-iodophenol, with 2,6-dinitro-4-ethylphenol. The dinitro-4-halophenols are present in amounts ranging from about 1.0% to 99% by weight of the mixture.

Generally, distillation is carried out in the presence of effective amounts of the polymerization inhibitor ranging from about 50 to 3,000 parts by weight of the inhibitor per million parts by weight of the vinyl aromatic monomer and preferrably in amounts ranging from about 100 to 1000 parts per million parts by weight of the vinyl monomer. The temperaturers at which the distillation is generally carried out ranges from about 40° C to 160° C, and depending on the particular monomer being distilled and the temperatures utilized, the amount of inhibitor added to the system will vary within the range stated.

With some monomers it may be desirable to use mixtures of the 2,6-dinitro-4-halophenols with 2,6-dinitro-4-ethylphenol, wherein the dinitro-4-halophenol is present in amounts ranging from about 1.0% to 99% by weight of the mixture. The mixture may be added to the distillation of the monomer in amounts ranging from about 100 to 1000 parts per million parts by weight of the vinyl aromatic monomer. As stated, 2,6-dinitro-4-ethylphenol has a melting point of about 36° C. and can be transported in the liquid form, i.e. at temperatures ranging from about 38° C. to 40° C. and metered directly into the distillation. Mixtures of 2,6-dinitro-4-ethylphenol and 2,6-dinitro-4-halophenol are liquid at ambient temperatures and can be metered in the same manner as 2,6,-dinitro-4-ethylphenol.

SPECIFIC EMBODIMENTS

Freshly distilled styrene, free of tertiary butyl catechol, was place in a round bottom flask equiped with a magnetic bar. Specific amounts of 4-chloro-2,6-dinitrophenol was added to the reactor with stirring. The reactor was closed and placed in a preheated oil bath held at 115°±1° C. and stirred for about four hours. A sample was withdrawn from the reactor, weighed and the amount of polymer formed was precipitated by the addition of absolute methanol (25 mls per 5 g of samples). The precipitate was filtered off, washed with cold methanol and dried. The degree of polymerization is shown in Table I.

TABLE I

Polymerization of styrene at 115 ± 1° C. in the presence of DNPEP, DNPC and DNP.

| | DNPEP ppm | DNPC ppm | DNPCP ppm | Polymerization % |
|---|---|---|---|---|
| 1. | 400 | — | — | 2.2 |
| 2. | — | 400 | — | 2.2 |
| 3. | 200 | 200 | — | 1.9 |
| 4. | 300 | 100 | — | 1.8 |
| 5. | — | — | 400 | 1.5 |

DNPEP is 2,6-dinitro-4-ethylphenol
DNPCP is 4-chloro-2,6-dinitrophenol
DNPC is 2,6-dinitro-paracresol As noted from the data in Table I, as the amount of dinitropara-ethylphenol increased to 300 ppm the percent of polymerization of the styrene dropped to 1.8%. However, at 400 parts per million of 4-chloro-2,6-dinitrophenol, the percent of polymerization decreased to 1.5%. It is evident from the data that the addition of 2,6-dinitro-4-halophenols alone or in combination with 2,6-dinitro-4-ethylphenol to the distillation of vinyl aromatic compounds not only lowers the cost and improves on the methods of using the inhibitors but also decreases the degree of polymerization of the monomer.

While this invention has been described by a specific embodiment, it is obvious that there are other modifications which can be made without departing from the spirit and scope of the invention as set forth in the appended claims.

Invention claimed is:

1. A process for inhibiting the polymerization of styrene and the alkyl substituted styrene monomers during the purification distillation of said monomers which comprises subjecting the monomers to distillation temperatures in the presence of inhibiting amounts of a mixture of 2,6-dinitro-4-chlorophenol and 2,6-dinitro-4-ethylphenol, wherein said chlorophenol is present in an amount ranging from 1% to 99% by weight of the mixture.

2. The process of claim 1 further characterized in that the amount needed to inhibit polymerization ranges from about 100 to 1,000 parts per million parts by weight of the monomer.

3. The process of claim 2 further characterized in that the distillation temperatures range from about 40° to 160° C.

4. The process of claim 3 is further characterized in that the monomer is styrene.

5. The process of claim 3 further characterized in that the monomer is an alkyl substituted styrene.